(12) United States Patent
Sommer-Knudsen et al.

(10) Patent No.: US 8,586,315 B2
(45) Date of Patent: *Nov. 19, 2013

(54) FLUORESCENT PROTEIN PARTICLES

(75) Inventors: Jens Sommer-Knudsen, Gordon (AU); David Moreland Gibbs, Turramurra (AU)

(73) Assignee: Innovative Purification Technologies Pty Ltd, Eveleigh (AU)

( * ) Notice: Subject to any disclaimer, the term of this patent is extended or adjusted under 35 U.S.C. 154(b) by 411 days.

This patent is subject to a terminal disclaimer.

(21) Appl. No.: 12/602,451

(22) PCT Filed: May 28, 2008

(86) PCT No.: PCT/AU2008/000748
§ 371 (c)(1),
(2), (4) Date: May 20, 2010

(87) PCT Pub. No.: WO2008/144817
PCT Pub. Date: Dec. 4, 2008

(65) Prior Publication Data
US 2010/0240146 A1    Sep. 23, 2010

(30) Foreign Application Priority Data

May 30, 2007    (AU) .................................. 2007902900

(51) Int. Cl.
*G01N 33/53* (2006.01)
(52) U.S. Cl.
USPC ........................................... 435/7.1; 435/7.2
(58) Field of Classification Search
None
See application file for complete search history.

(56) References Cited

U.S. PATENT DOCUMENTS 7,655,412 B2 *    2/2010    Mackenzie et al. ............ 435/7.1

FOREIGN PATENT DOCUMENTS

WO    WO 02/094259    11/2002
WO    WO 2004/088313    10/2004

OTHER PUBLICATIONS

Ellson et al. (Nature Cell Biology 2001 vol. 3, p. 679-682).*
Heinzel et al. (J. Immunology 1997 vol. 158, p. 4381-4388).*
King et al. "Protein-only transmission of three yeast prion strains", Nature, 428, pp. 319-323, 2004.
Kar et al., "Assembly and Intracellular Localization of the Bluetongue Virus Core Protein VP3", Journal of Virology, 79, pp. 11487-11495, 2005.
Lu et al., "Cloning, Expression, Purfication, and Characterization of LC-1 ScFv with CFP Tag", Journal of Zhejiang University Science, 6, pp. 832-837, 2005.
Seo et al., "Baculoviral Polyhedrin as a Novel Fusion Partner for Formation of Inclusion Body . . . ", Biotechnology and Bioengineering, 84, pp. 467-473, 2003.
O'Farrell et al., "Transfected Synphilin-1 Forms Cytoplasmic Inclusions in HEK293 Cells", Molecular Brain Research, 97, pp. 94-102, 2001.
Geertsma et al., "Quality Control of Overexpressed . . . ", Proceedings of the National Academy of Sciences USA, 105, pp. 5722-5727, 2008.
Takahashi et al., "Detection of Polyglutamine Protein Oligomers in Cells by Fluorescence . . . ", Journal of Biological Chemistry, 282, pp. 24039-24048, 2007.

* cited by examiner

*Primary Examiner* — Jacob Cheu
(74) *Attorney, Agent, or Firm* — Morgan, Lewis & Bockius LLP

(57) ABSTRACT

A fluorescent protein particle comprising: a particle forming component capable of forming or aggregating into a substantially insoluble protein particle when expressed by a cell; a fluorescent component; and a functional component capable of binding to, or being bound by, a target.

15 Claims, 6 Drawing Sheets

Key:
1. NGFPNPANLCP40 Soluble 20 µl
2. NGFPNPANLCP40 Insoluble 20 µl
3. NeGFPNPANLCP40 Soluble 20 µl
4. NeGFPNPANLCP40 Insoluble 20 µl
5. pDuet only Insoluble 20 µl
6. Novex Marker (10 µl)

Expected size:
NGFPNLCPACP40    65.6 kDa, pI 5.5
NeGFPNLCPACP40   65.6 kDa, pI 5.5

```
     NGFPF
        NcoI
aaaaccATGGttAGTAAAGGAGAAGAACTTTTCACTGGAGTTGTCCCAATTCTTGTTGAATTAGATGGTGATGTTAATGGGCACAAATTTTCTGTCAGTG
   1 ---------+----------+----------+----------+----------+----------+----------+----------+----------
     +
ttttggTACCaaTCATTTCCTCTTCTTGAAAAGTGACCTCAACAGGGTTAAGAACAACTTAATCTACCACTACAATTACCCGTGTTTAAAAGACAGTCAC
      K T M V S K G E E L F T G V V P I L V E L D C D V N G H K F S V S
G
                                                                NGFPINTF
                                                                   NcoI
                                                               Changed residue
GAGAGGGTGAAGGTGATGCAACATACGGAAAACTTACCCTTAAATTTATTTGCACTACTGGAAAACTACCTGTTCCgTGGCCAACACTTGTCACTACTTT
 101 ---------+----------+----------+----------+----------+----------+----------+----------+----------
     +
CTCTCCCACTTCCACTACGTTGTATGCCTTTTGAATGGGAATTTAAATAAACGTGATGACCTTTTGATGGACAAGGcACCGGTTGTGAACAGTGATGAAA
      E G E G D A T Y G K L T L K F I C T T G K L P V P W P T L V T T F
                                                     NGFPINTR
CTCTTATGGTGTTCAATGCTTTTCAAGATACCCAGATCATATGAAACGGCATGACTTTTTCAAGAGTGCCATGCCCGAAGGTTATGTACAGGAAAGAACT
 201 ---------+----------+----------+----------+----------+----------+----------+----------+----------
     +
GAGAATACCACAAGTTACGAAAAGTTCTATGGGTCTAGTATACTTTGCCCGTACTGAAAAAGTTCTCACGGTACGGGCTTCCAATACATGTCCTTTCTTGA
      S Y G V Q C F S R Y P D H M K R H D F F K S A M P E G Y V Q E R T ATATTTTTCAAAGATGACGGGAACTACAAGACACGTGCTGAAGTCAAGTTTGAAGGTGATACCCTTGTTAATAGAATCGAGTTAAAAGGTATTGATTTTA
 301 ---------+----------+----------+----------+----------+----------+----------+----------+----------
     +
TATAAAAAGTTTCTACTGCCCTTGATGTTCTGTGCACGACTTCAGTTCAAACTTCCACTATGGGAACAATTATCTTAGCTCAATTTTCCATAACTAAAAT
      I F F K D D G N Y K T R A E V K F E G D T L V N R I E L K G I D F
K
AAGAAGATGGAAACATTCTTGGACACAAATTGGAATACAACTATAACTCACACAATGTATACATCATGGCAGACAAACAAAAGAATGGAATCAAAGTTAA
 401 ---------+----------+----------+----------+----------+----------+----------+----------+----------
     +
TTCTTCTACCTTTGTAAGAACCTGTGTTTAACCTTATGTTGATATTGAGTGTGTTACATATGTAGTACCGTCTGTTTGTTTTCTTACCTTAGTTTCAATT
      E D G N I L G H K L E Y N Y N S H N V Y I M A D K Q K N G I K V N CTTCAAAATTAGACACAACATTGAAGATGGAAGCGTTCAACTAGCAGACCATTATCAACAAAATACTCCAATTGGCGATGGCCCTGTCCTTTTACCAGAC
 501 ---------+----------+----------+----------+----------+----------+----------+----------+----------
     +
GAAGTTTTAATCTGTGTTGTAACTTCTACCTTCGCAAGTTGATCGTCTGGTAATAGTTGTTTTATGAGGTTAACCGCTACCGGGACAGGAAAATGGTCTG
      F K I R H N I E D G S V Q L A D H Y Q Q N T P I G D G P V L L P D AACCATTACCTGTCCACACAATCTGCCCTTTCGAAAGATCCCAACGAAAAGAGAGACCACATGGTCCTTCTTGAGTTTGTAACAGCTGCTGGGATTACAC
 601 ---------+----------+----------+----------+----------+----------+----------+----------+----------
     +
TTGGTAATGGACAGGTGTGTTAGACGGGAAAGCTTTCTAGGGTTGCTTTTCTCTCTGGTGTACCAGGAAGAACTCAAACATTGTCGACGACCCTAATGTG
      N H Y L S T Q S A L S K D P N E K R D H M V L L E F V T A A G I T
H
                                     NcoI
     ATGGCATGGATGAACTATACAAAGGAGGCGGCtccatggtttt
 701 ---------+----------+----------+---------+--- 743
     TACCGTACCTACTTGATATGTTTCCTCCGCCGaggtaccaaaa
       G M D E L Y K G G G S M V
                     NGFPR
```

Figure 7

```
             10                  30                  50
MVSKGEELFTGVVPILVELDGDVNGHKFSVSGEGEGDATYGKLTLKFICTTGKLPVPWPT
             70                  90                 110
LVTTFSYGVQCFSRYPDHMKRHDFFKSAMPEGYVQERTIFFKDDGNYKTRAEVKFEGDTL
            130                 150                 170
VNRIELKGIDFKEDGNILGHKLEYNYNSHNVYIMADKQKNGIKVNFKIRHNIEDGSVQLA
            190                 210                 230
DHYQQNTPIGDGPVLLPDNHYLSTQSALSKDPNEKRDHMVLLEFVTAAGITHGMDELYKG
            250                 270                 290
GGSMVTPAANAAQHDEAVDNKFNKEQQNAFYEILHLPNLNEEQRNAFIQSLKDDPSQSAN
            310                 330                 350
LLAEAKKLNDAQAPKVDNKFNKEQQNAFYEILHLPNLNEEQRNAFIQSLKDDPSQSANLL
            370                 390                 410
AEAKKLNDAQASLGGGGSGGGGSGGGGSGSVFPATRTYACYVDGKVHGNGGDLNMINPAC
            430                 450                 470
LDALAISGNYQFWNWFGNLISNAGGRHREIIPDGKLCGPTASFDGMNQARTDWWTTRLQP
            490                 510                 530
GATITVRVNAWAPHPGTWYLYVTRDGWDPTQPLKWSDLGPTPFSQVTNPPINSSGPDGAE
            550                 570                 590
YSWQVQLPNKQGRHIIYMIWQRSDSPEAFYNCSDVYFGSGPIAYEFGDPREGG*
```

US 8,586,315 B2

SEQUENCE LISTING

```
<160> NUMBER OF SEQ ID NOS: 7

<210> SEQ ID NO 1
<211> LENGTH: 1486
<212> TYPE: DNA
<213> ORGANISM: Artificial
<220> FEATURE:
<223> OTHER INFORMATION: Synthetic sequence

<400> SEQUENCE: 1
aaaaccatgg ttagtaaagg agaagaactt ttcactggag ttgtcccaat tcttgttgaa      60
ttagatggtg atgttaatgg gcacaaattt tctgtcagtg ttttggtacc aatcatttcc     120
tcttcttgaa aagtgacctc aacagggtta agaacaactt aatctaccac tacaattacc     180
cgtgtttaaa agacagtcac gagagggtga aggtgatgca acatacggaa aacttaccct     240
taaatttatt tgcactactg gaaaactacc tgttccgtgg ccaacacttg tcactacttt     300
ctctcccact tccactacgt tgtatgcctt ttgaatggga atttaaataa acgtgatgac     360
cttttgatgg acaaggcacc ggttgtgaac agtgatgaaa ctcttatggt gttcaatgct     420
```

```
tttcaagata cccagatcat atgaaacggc atgactttt  caagagtgcc atgcccgaag    480
gttatgtaca ggaaagaact gagaatacca caagttacga aaagttctat gggtctagta    540
tactttgccg tactgaaaaa gttctcacgg tacgggcttc aatacatgt  cctttcttga    600 atattttca  aagatgacgg aactacaag  acacgtgctg aagtcaagtt tgaaggtgat    660
acccttgtta atagaatcga gttaaaaggt attgatttta tataaaagt  ttctactgcc    720 cttgatgttc tgtgcacgac ttcagttcaa acttccacta tgggaacaat tatcttagct    780
caattttcca taactaaaat aagaagatgg aaacattctt ggacacaaat tggaatacaa    840
ctataactca cacaatgtat acatcatggc agacaaacaa agaatggaa  tcaaagttaa    900 ttcttctacc tttgtaagaa cctgtgttta accttatgtt gatattgagt gtgttacata    960
tgtagtaccg tctgtttgtt tcttaccttt agtttcaatt cttcaaaatt agacacaaca   1020
ttgaagatgg aagcgttcaa ctagcagacc attatcaaca aaatactcca attggcgatg   1080
gccctgtcct tttaccagac gaagttttaa tctgtgttgt aacttctacc ttcgcaagtt   1140
gatcgtctgg taatagttgt tttatgaggt taaccgctac cgggacagga aaatggtctg   1200
aaccattacc tgtccacaca atctgccctt tcgaaagatc ccaacgaaaa gagagaccac   1260
atggtccttc ttgagtttgt aacagctgct gggattacac ttggtaatgg acaggtgtgt   1320
tagacgggaa agctttctag ggttgctttt ctctctggtg taccaggaag aactcaaaca   1380
ttgtcgacga ccctaatgtg atggcatgga tgaactatac aaaggaggcg ctccatggt    1440 ttttaccgta cctacttgat atgtttcctc cgccgaggta ccaaaa                  1486
```

<210> SEQ ID NO 2
<211> LENGTH: 247
<212> TYPE: PRT
<213> ORGANISM: Artificial
<220> FEATURE:
<223> OTHER INFORMATION: Synthetic sequence

<400> SEQUENCE: 2

```
Lys Thr Met Val Ser Lys Gly Glu Glu Leu Phe Thr Gly Val Val Pro
1               5                   10                  15

Ile Leu Val Glu Leu Asp Gly Asp Val Asn Gly His Lys Phe Ser Val
            20                  25                  30

Ser Gly Glu Gly Glu Gly Asp Ala Thr Tyr Gly Lys Leu Thr Leu Lys
        35                  40                  45

Phe Ile Cys Thr Thr Gly Lys Leu Pro Val Pro Trp Pro Thr Leu Val
    50                  55                  60

Thr Thr Phe Ser Tyr Gly Val Gln Cys Phe Ser Arg Tyr Pro Asp His
65                  70                  75                  80

Met Lys Arg His Asp Phe Phe Lys Ser Ala Met Pro Glu Gly Tyr Val
                85                  90                  95

Gln Glu Arg Thr Ile Phe Phe Lys Asp Asp Gly Asn Tyr Lys Thr Arg
            100                 105                 110

Ala Glu Val Lys Phe Glu Gly Asp Thr Leu Val Asn Arg Ile Glu Leu
        115                 120                 125

Lys Gly Ile Asp Phe Lys Glu Asp Gly Asn Ile Leu Gly His Lys Leu
    130                 135                 140

Glu Tyr Asn Tyr Asn Ser His Asn Val Tyr Ile Met Ala Asp Lys Gln
145                 150                 155                 160

Lys Asn Gly Ile Lys Val Asn Phe Lys Ile Arg His Asn Ile Glu Asp
                165                 170                 175
```

```
Gly Ser Val Gln Leu Ala Asp His Tyr Gln Gln Asn Thr Pro Ile Gly
            180                 185                 190

Asp Gly Pro Val Leu Leu Pro Asp Asn His Tyr Leu Ser Thr Gln Ser
        195                 200                 205

Ala Leu Ser Lys Asp Pro Asn Glu Lys Arg Asp His Met Val Leu Leu
    210                 215                 220

Glu Phe Val Thr Ala Ala Gly Ile Thr His Gly Met Asp Glu Leu Tyr
225                 230                 235                 240

Lys Gly Gly Gly Ser Met Val
                245

<210> SEQ ID NO 3
<211> LENGTH: 593
<212> TYPE: PRT
<213> ORGANISM: Artificial
<220> FEATURE:
<223> OTHER INFORMATION: Synthetic sequence

<400> SEQUENCE: 3

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys Gly
225                 230                 235                 240

Gly Gly Ser Met Val Thr Pro Ala Ala Asn Ala Gln His Asp Glu
                245                 250                 255

Ala Val Asp Asn Lys Phe Asn Lys Glu Gln Gln Asn Ala Phe Tyr Glu
            260                 265                 270

Ile Leu His Leu Pro Asn Leu Asn Glu Glu Gln Arg Asn Ala Phe Ile
        275                 280                 285

Gln Ser Leu Lys Asp Asp Pro Ser Gln Ser Ala Asn Leu Leu Ala Glu
```

```
                290                 295                 300
Ala Lys Lys Leu Asn Asp Ala Gln Ala Pro Lys Val Asp Asn Lys Phe
305                 310                 315                 320

Asn Lys Glu Gln Gln Asn Ala Phe Tyr Glu Ile Leu His Leu Pro Asn
                325                 330                 335

Leu Asn Glu Glu Gln Arg Asn Ala Phe Ile Gln Ser Leu Lys Asp Asp
            340                 345                 350

Pro Ser Gln Ser Ala Asn Leu Leu Ala Glu Ala Lys Lys Leu Asn Asp
        355                 360                 365

Ala Gln Ala Ser Leu Gly Gly Gly Ser Gly Gly Gly Ser Gly
    370                 375                 380

Gly Gly Gly Ser Gly Ser Val Phe Pro Ala Thr Arg Thr Tyr Ala Cys
385                 390                 395                 400

Tyr Val Asp Gly Lys Val His Gly Asn Gly Asp Leu Asn Met Ile
                405                 410                 415

Asn Pro Ala Cys Leu Asp Ala Leu Ala Ile Ser Gly Asn Tyr Gln Phe
                420                 425                 430

Trp Asn Trp Phe Gly Asn Leu Ile Ser Asn Ala Gly Gly Arg His Arg
            435                 440                 445

Glu Ile Ile Pro Asp Gly Lys Leu Cys Gly Pro Thr Ala Ser Phe Asp
450                 455                 460

Gly Met Asn Gln Ala Arg Thr Asp Trp Trp Thr Arg Leu Gln Pro
465                 470                 475                 480

Gly Ala Thr Ile Thr Val Arg Val Asn Ala Trp Ala Pro His Pro Gly
                485                 490                 495

Thr Trp Tyr Leu Tyr Val Thr Arg Asp Gly Trp Asp Pro Thr Gln Pro
            500                 505                 510

Leu Lys Trp Ser Asp Leu Gly Pro Thr Pro Phe Ser Gln Val Thr Asn
        515                 520                 525

Pro Pro Ile Asn Ser Ser Gly Asp Gly Ala Glu Tyr Ser Trp Gln
    530                 535                 540

Val Gln Leu Pro Asn Lys Gln Gly Arg His Ile Ile Tyr Met Ile Trp
545                 550                 555                 560

Gln Arg Ser Asp Ser Pro Glu Ala Phe Tyr Asn Cys Ser Asp Val Tyr
                565                 570                 575

Phe Gly Ser Gly Pro Ile Ala Tyr Glu Phe Gly Asp Pro Arg Glu Gly
                580                 585                 590

Gly

<210> SEQ ID NO 4
<211> LENGTH: 34
<212> TYPE: DNA
<213> ORGANISM: Artificial
<220> FEATURE:
<223> OTHER INFORMATION: Synthetic sequence

<400> SEQUENCE: 4
aaaaccatgg ttagtaaagg agaagaactt ttca                              34

<210> SEQ ID NO 5
<211> LENGTH: 29
<212> TYPE: DNA
<213> ORGANISM: Artificial
<220> FEATURE:
<223> OTHER INFORMATION: Synthetic sequence

<400> SEQUENCE: 5
```

-continued

```
aaaaccatgg agccgcctcc tttgtatag                                              29

<210> SEQ ID NO 6
<211> LENGTH: 28
<212> TYPE: DNA
<213> ORGANISM: Artificial
<220> FEATURE:
<223> OTHER INFORMATION: Synthetic sequence

<400> SEQUENCE: 6
acctgttccg tggccaacac ttgtcact                                               28

<210> SEQ ID NO 7
<211> LENGTH: 27
<212> TYPE: DNA
<213> ORGANISM: Artificial
<220> FEATURE:
<223> OTHER INFORMATION: Synthetic sequence

<400> SEQUENCE: 7
ttggccacgg aacaggtagt tttccag                                                27
```

FLUORESCENT PROTEIN PARTICLES

RELATED APPLICATIONS

The present application is a U.S. National Phase Application of International Application No. PCT/AU2008/000748 (filed May 28, 2008) which claims the benefit of Australian Patent Application No. 2007902900 (filed May 30, 2007), both of which are hereby incorporated by reference in their entireties.

SEQUENCE LISTING SUBMISSION VIA EFS-WEB

A computer readable text file, entitled "057734-5026-US-SeqListing.txt," created on or about May 18, 2010 with a file size of about 11 kb contains the sequence listing for this application and is hereby incorporated by reference in its entirety.

TECHNICAL FIELD

The present invention relates to fluorescent protein particles and uses thereof.

BACKGROUND OF THE INVENTION

Insoluble fluorescent particles with targets such as ligands, proteins or peptides capable of binding to a desired molecule or biological entity displayed on the surface have uses in biological applications. At present, such particles are typically prepared by first forming a particle of a suitable material such as an organic polymer, wherein a low molecular weight fluorescent molecule is incorporated, coating this particle with a hydrophilic polymer, attaching chemically active groups to this material and then in turn immobilising the desired peptide or protein in a purified form to the particle through reaction with the chemically active groups. The production of such particles is often cumbersome and expensive as it typically involves several steps, including formation of the fluorescent particles themselves, activation of these particles, synthesis or purification of the desired peptide or protein as well as the step of immobilising the purified peptide or protein to the particle.

The present inventors have found that useful fluorescent protein particles can be made that have applications which include analytical and diagnostic applications.

SUMMARY OF THE INVENTION

In a first aspect, the present invention provides a fluorescent protein particle comprising:
a particle forming component capable of forming or aggregating into a substantially insoluble protein particle when expressed by a cell;
a fluorescent component; and
a functional component capable of binding to, or being bound by, a target.

The particle forming component of the protein can be obtained or derived from any suitable protein that can self-assemble into particles when expressed in a cell. The particle may be formed by a structured assembly of the protein or it may form an aggregate such as known from inclusion bodies. It will be appreciated that the particle forming component may be a known protein or part thereof or an artificially formed protein or peptide. Preferably, the particle forming component is the protein p40, alpha-amylase, human alpha-fetoprotein, Somatotropin, cellulose binding domain from Clostridium, particle forming parts thereof, or other proteins which form or aggregate into a suitable particle when expressed in an appropriate host microorganism such as *Escherichia coli*.

The fluorescent component may be a fluorescent protein such as Green Fluorescent Protein (GFP). Examples of fluorescent proteins include, but not limited, to green fluorescent protein (GFP), Enhanced Green Fluorescent Protein (eGFP), Blue Fluorescent Protein (BFP), Yellow Fluorescent Protein (YFP), Cyan Fluorescent Protein (CFP), Red Fluorescent Protein (RFP), or any other suitable fluorescent protein, or combination thereof, or fluorescent parts or derivatives thereof.

Preferably, the fluorescent protein is green fluorescent protein (GFP) or fluorescent part or derivative thereof.

The protein particle may comprise one or more functional components capable of binding to, or being bound by, two or more targets.

The functional component of the particle may comprise an antibody binding domain such as protein A, protein G, protein L, an antibody, an antibody binding domain, a single chain antibody, avidin, streptavidin, an enzyme, an inhibitor, an antigenic determinant, an epitope, a binding site, a lectin, a polyhistidine, an oligohistidine, a receptor, a hormone, a signalling molecule, a polypeptide with specific or group specific binding capabilities, or any combination thereof.

Preferably, the functional component is protein A, protein G, protein L or active fragment thereof.

The target can be a ligand, compound or biological entity such as a protein, a peptide, a polypeptide, an immunoglobulin, biotin, an inhibitor, a co-factor, an enzyme, a receptor, a monosaccharide, an oligosaccharide, a polysaccharide, a glycoprotein, a lipid; a nucleic acid, a hormone, a toxin or any other molecule, a cell or fragment thereof, an organelle, a virus, a bacterium, a fungus, a protist, a parasite, an animal, a plant or any substructure, fragments or combinations thereof.

In a second aspect, the present invention provides a chimeric nucleic acid molecule encoding a fluorescent protein particle comprising:
a nucleic acid molecule encoding an aggregating protein component;
a nucleic acid molecule encoding a fluorescent protein component; and
a nucleic acid molecule encoding a protein functional component capable of binding to, or being bound by, a target.

When the recombinant, chimeric nucleic acid molecule is expressed in a cell, a fluorescent protein particle capable of binding to, or being bound by, a target is formed.

In a third aspect, the present invention provides a vector comprising a chimeric nucleic acid molecule according to the second aspect of the present invention.

In a fourth aspect, the present invention provides a method of forming a fluorescent protein particle capable of binding to; or being bound by, a target comprising:
providing a chimeric nucleic acid molecule according to the second aspect of the present invention or a vector according to the third aspect of the present invention to a cell; and
allowing the cell to express the nucleic acid molecule to form an insoluble fluorescent protein particle.

Preferably, the method further comprises:
recovering the insoluble fluorescent protein particle.

The recombinant, chimeric nucleic acid molecule can be provided in any suitable construct such as vector, plasmid, virus, or any other suitable vehicle.

In a fifth aspect, the present invention provides a fluorescent protein particle produced according to the method of the fourth aspect of the present invention.

In a sixth aspect, the present invention provides a fluorescent protein particle for detecting or quantifying at least one target component comprising:

a recombinant fluorescent protein particle comprising an aggregating component capable of forming or aggregating into an insoluble protein particle when expressed by a cell;

a fluorescent protein component; and a functional component capable of binding to, or being bound by, a target.

The functional component may comprise protein A, protein G, protein L, an antibody, an antibody binding domain, a single chain antibody, avidin, streptavidin, an enzyme, an inhibitor, an antigenic determinant, an epitope, a binding site, a lectin, a cellulose binding protein, a polyhistidine, an oligohistidine, a receptor, a hormone, a signalling molecule, a polypeptide with specific or group specific binding capabilities, or any combination thereof.

The protein particle is preferably produced by recombinant DNA technology.

In a seventh aspect, the present invention provides a method for detecting a target in a sample comprising:

providing a fluorescent protein particle according to the first, fifth or sixth aspects of the present invention to a sample;

allowing the fluorescent protein particle to bind to a target in the sample; and detecting any fluorescent particles bound to the target in the sample.

The sample or components in the sample may be immobilised onto a surface. Immobilization can be carried out by means of adsorption onto a plastic surface such as a microtitre plate, by a dot, slot, or Western blot onto a membrane, or by any other suitable means.

When a fluorescent protein particle according to the present invention is added to a sample, the target is selectively bound by the functional component of the protein particle.

The sample may include blood, blood plasma, blood serum, human, animal, plant, or microbial cultures, extracts or secretions, air, water, or soil samples or extracts, or any combination thereof.

The sample may be a non-liquid sample which has been fixed or embedded in a suitable medium or otherwise prepared by standard techniques for microscopical analysis.

The target component may comprise a protein, a peptide, a polypeptide, an immunoglobulin, biotin, biotin derivatives, an inhibitor, a co-factor, a substrate, an enzyme, a receptor, a monosaccharide; an oligosaccharide, a polysaccharide, a glycoprotein, a lipid, a nucleic acid, a cell or fragment thereof, an organelle, a virus, a parasite, a fungus, a toxin, a hormone, a serum protein, a milk protein, macromolecule or any other molecule or any combination or fraction thereof.

When a fluorescent protein particle according to the invention is added to a solid sample, the target component or biological entity is selectively bound by the functional component of the protein particle. The sample may comprise human, animal, plant, or microbial organs, tissues, or cultures, extracts, or secretions, soil samples or extracts, or any combination thereof. The target component may comprise a protein, a peptide, a polypeptide, an immunoglobulin, biotin, biotin derivatives, an inhibitor, a co-factor, a substrate, an enzyme, a receptor, a monosaccharide, an oligosaccharide, a polysaccharide, a glycoprotein, a lipid, a nucleic acid, a cell or fragment thereof, an organelle, a virus, a parasite, a fungus, a toxin, a hormone, a serum protein, a milk protein, macromolecule or any other molecule or any combination or fraction thereof.

In a eighth aspect, the present invention provides use of the fluorescent protein particle according to the first, fifth or sixth aspects of the present invention in a diagnostic, analytical or detection application.

A suitable diagnostic, analytical or detection application is cytometry such as flow cytometry.

In a ninth aspect, the present invention provides a kit for diagnostic or analytical procedure comprising:

a fluorescent protein particle according to the first, fifth or sixth aspects of the present invention; and suitable diluent or reagent.

In a preferred form, the kit further contains instructions to carry out a diagnostic procedure.

An advantage of the present invention is the ability to produce recombinantly and recover the particles when made by a cell. For example, the particles can be recovered by centrifugation, sedimentation or filtration.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form component of the prior art base or were common general knowledge in the field relevant to the present invention as it existed in Australia prior to development of the present invention.

In order that the present invention may be more clearly understood, preferred embodiments will be described with reference to the following drawings and examples.

BRIEF DESCRIPTION OF THE DRAWINGS

FIG. 2 shows depictions of PCR products and plasmids. A Linear depiction of GFP and eGFP showing relative positions of oligonucleotide primer binding sites and the naturally occurring NcoI restriction enzyme site. B Linear depiction of the PCR products generated by overlap extension PCR to remove the internal NcoI site. C A linear depiction of the cassette region of the of the plasmid pDuet:NPANLCP40. D A linear depiction of the cassette region of the of the plasmids pDuet:NGFPNPANLCP40 and pDuet:NeGFPNPANLCP40.

MODES(S) FOR CARRYING OUT THE INVENTION

Definitions

The term "particle" as used herein refers to a substantially insoluble entity comprising protein. These entities may be spherical, ellipsoidal, in string form, in sheets, discs or any other shape. The particles may be of any size between about 1 nm and 100 μm.

The term "polypeptide" as used herein means a polymer made up of amino acids linked together by peptide bonds, and includes fragments or analogues thereof. The terms "polypeptide" and "protein" are used interchangeably herein, although for the purposes of the present invention a "polypeptide" may constitute a portion of a full length protein or a complete full length protein.

The term "nucleic acid" as used herein refers to a single- or double-stranded polymer of deoxyribonucleotide, ribonucleotide bases or known analogues of natural nucleotides, or mixtures thereof. The term includes reference to a specified sequence as well as to a sequence complimentary thereto, unless otherwise indicated. The terms "nucleic acid" and "polynucleotide" are used herein interchangeably.

The term "variant" as used herein refers to substantially similar sequences. Generally, polypeptide sequence variant possesses qualitative biological activity in common. Further, these polypeptide sequence variants may share at least 50%, 55%, 60%, 65%, 70%, 75%, 80%, 85%, 90%, 95%, 96%, 97%, 98% or 99% sequence identity. Also included within the meaning of the term "variant" are homologues of polypeptides of the invention. A homologue is typically a polypeptide from a different species but sharing substantially the same biological function or activity as the corresponding polypeptide disclosed herein. Variant therefore can refer to a polypeptide which is produced from the nucleic acid encoding a polypeptide, but differs from the wild type polypeptide in that it is processed differently such that it has an altered amino acid sequence. For example a variant may be produced by an alternative splicing pattern of the primary RNA transcript to that which produces a wild type polypeptide.

The term "fragment" refers to a polypeptide molecule that encodes a constituent or is a constituent of a polypeptide of the invention or variant thereof. Typically the fragment possesses qualitative biological activity in common with the polypeptide of which it is a constituent. The term "fragment" therefore refers to a polypeptide molecule that is a constituent of a full-length polypeptide and possesses at least some qualitative biological activity in common with the full-length polypeptide. The fragment may be derived from the full-length polypeptide or alternatively may be synthesised by some other means, for example chemical synthesis.

The term "substantially" as used herein means the majority but not necessarily all, and thus in relation to a modified polypeptide "substantially" lacking a component region of a corresponding wild-type polypeptide, the modified polypeptide may retain a portion of that component region. For example, a modified polypeptide "substantially" lacking a component region of a corresponding wild-type polypeptide may retain approximately 50 percent or less of the sequence of the component region, although typically the component region is rendered structurally and/or functionally inactive by virtue of the proportion of the sequences of the region omitted.

The term "chimeric protein" as used herein means a protein produced by expression of a recombinant DNA molecule encoding a protein having at least two parts, one component capable of forming or aggregating into an insoluble particle and at least a second component capable of fluorescence or binding to a target molecule or biological entity. The term also covers a protein produced by expression of a recombinant DNA sequence encoding a protein having at least three parts; one component capable of forming a particle, a second component capable of fluorescence, and a third component capable of binding to a target molecule or biological entity Outline The present invention is predicated on the finding that insoluble particles of peptides or proteins are capable of performing a diagnostic or analytical function can be obtained through expression of chimeric recombinant proteins where one component of the protein is capable of forming an insoluble particle a second component is capable of fluorescence and a third component is capable of binding to a target molecule or biological entity. These self-assembling structures/particles can be made by forming a nucleic acid, typically DNA, construct encoding a peptide/protein chain which will form an insoluble particle. The nucleic acid further contains a sequence encoding at least one further protein or peptide capable of fluorescence as well as at least one further sequence encoding a protein or peptide chain capable of binding to a target such as ligand, compound or biological entity. When this DNA construct is placed in a suitable host organism, the protein particle is expressed.

Alternatively, these self assembling structures/particles can be made by producing two nucleic acid constructs encoding two separate peptide/protein chains, one construct encoding a peptide/protein chain which will form an insoluble particle linked with a sequence encoding a fluorescent protein and one construct encoding a peptide/protein chain which will form an insoluble particle linked with a sequence encoding a peptide/protein chain capable of binding to a target such as a target molecule or biological entity. These constructs can be co-expressed in a suitable host organism such that particles having both a fluorescent protein and a peptide/protein capable of binding a target molecule or biological entity on the same particle will be formed. The self-assembling protein component of the particles according to the present invention may be a peptide/protein known to form inclusion bodies (IB) when expressed in a suitable manner in a suitable host, or it may be a specially designed sequence capable of forming an insoluble particle having the desired characteristics.

The nucleotide sequences may or may not be interspaced by a sequence encoding a "spacing" peptide or protein sequence. The size of the structures/particles would depend on the length of the engineered protein chain an may be in the range of about 1 nm to 5 μm if expressed and assembled inside the producing cell and up to several hundred micrometer if assembled outside the cell such as when the protein chains are secreted into the medium surrounding the cells (e.g. by including a nucleotide sequence encoding a secretion signal peptide) or when the structures are assembled in vitro.

The structures may be made up of heterologous proteins with different protein particle-forming amino acid sequences and/or different peptide/protein domains capable of binding to different targets such that each of these structures will be able to bind to more than one target molecule or biological structure.

The host organism for expressing the protein may be a prokaryotic organism or a eukaryotic organism. The prokaryotic organism may be a bacterium and the eukaryotic organism may be a yeast, a fungus, a protist, a plant, an animal, or cultures or any combination thereof.

While it is expected that these self assembling protein particles have a wide range of applications, it has been found that these particles can be used for diagnostic and analytical applications.

Self Assembling Protein Particles

Functional, self assembling proteinaceous particles can be prepared by providing a nucleic acid construct or vector encoding a chimeric protein where one component is capable of forming or aggregating into an insoluble particle, a further component is capable of fluorescence, and yet a further component is capable of binding to a target, expressing the construct or constructs in a suitable host organism and preferably recovering said particles from said host organism.

Vectors

The vector for the production of the fluorescent protein particle could include, though not be limited to, a plasmid, a phagemid, a bacterial artificial chromosome (BAC), a yeast artificial chromosome, a FOSMID, or a COSMID.

The vector may function and replicate as an independent extrachromosomal element, or it could be integrated at any position into the genome of the expression host. It should be appreciated by persons skilled in the art that a variety of vectors could be designed, constructed and used to produce a recombinant fluorescent protein particle.

Recombinant Protein Particle Production

Preferably, the vector would include the chimeric gene or genes encoding the protein that will form the fluorescent protein particle, a constitutive or inducible promoter to drive expression of the protein, a selectable phenotypic marker, such as a gene encoding resistance to an antibiotic.

Host Microorganisms

A variety of organisms, both eukaryotic and prokaryotic, both unicellular and multicellular, can be genetically engineered and employed as recombinant expression hosts for the production of a recombinant protein or proteins. A person skilled in the art would appreciate that suitable the chimeric proteins described herein could be successfully produced in a variety of recombinant host systems.

Chimeric Proteins

The present invention provides production of recombinant chimeric proteins that have been modified to contain at least one component that forms or aggregates into an insoluble particle, at least one component that is capable of fluorescence, and at least one component that is capable of binding to a target molecule or biological structure. Alternatively the particles according to the present invention can be produced by co-expressing two separate chimeric proteins one of which has a particle forming component linked to a fluorescent protein and one which has a particle forming component linked to a protein capable of binding to a target molecule or biological structure. Typically these proteins are created by recombinant DNA technology where nucleotide fragments encoding the desired proteins, peptides or fragments thereof are joined together with or without an interspaced nucleotide fragment encoding a spacer or linker region. The particle forming component of the protein may be P40 or any other protein such as Alpha-amylase, human alpha-fetoprotein, Somatotropin, cellulose binding domain from clostridium, or other proteins, which forms or aggregates into a suitable particle when expressed in an appropriate host organism such as *Escherichia coli*, one other component may be green fluorescent protein (GFP), Enhanced green fluorescent protein (eGFP), Blue Fluorescent Protein (BFP), Yellow Fluorescent Protein (YFP), Cyan Fluorescent Protein (CFP), Red Fluorescent Protein (RFP), or any other suitable fluorescent protein, and the target binding component of the protein may comprise an antibody binding domain such as protein. A, protein G, protein L, an antibody, an antibody binding domain, a single chain antibody, avidin, streptavidin, an enzyme, an inhibitor, an antigenic determinant, an epitope, a binding site, a lectin, a polyhistidine, an oligohistidine, a receptor, a hormone, a signalling molecule, a polypeptide with specific or group specific binding capabilities, or any combination thereof.

Analytical and Diagnostic Applications

An example of an application of the present invention is based on the finding that these self assembling protein particles can be used for analytical and diagnostic applications thus providing for fast, effective, and relatively inexpensive and reliable analytical applications and diagnostic tests. The particular instances of analytical and diagnostic tests and applications exemplified herein is readily understood and appreciated by persons skilled in the art as representing general methods of analysing, detecting, and quantifying molecules or biological structures of interest.

Accordingly, the present invention in a preferred form relates to the quantification of target molecules or biological entities. The analytical or diagnostic particle comprises at least one protein component capable of forming an insoluble particle, at least one component capable of fluorescence, and at least one Component able to bind the target molecule or biological entity of interest. When a protein particle according to the present invention is contacted with a sample containing a mixture of components, the particle selectively binds to a target molecule or biological entity.

Thus, binding of the protein particle to the target molecule or biological entity, followed by removal of unbound particles, allows for detection and quantification of the target molecule or biological entity through fluorescence analysis, as there is a positive correlation between fluorescent signal and concentration of target molecules in the sample.

Targets

The target may be a ligand, protein, a peptide, a polypeptide, an immunoglobulin, biotin, an inhibitor, a co-factor, an enzyme, a receptor, a monosaccharide, an oligosaccharide, a polysaccharide, a glycoprotein, a lipid, a nucleic acid, a hormone, a toxin or any other molecule, a cell or fragment thereof, an organelle, a virus, a bacterium, a fungus, a protist, a parasite, an animal, a plant or any substructure, fragments or combinations thereof.

Samples

Samples for analysis may comprise blood, blood plasma, blood serum, human, animal, plant, or microbial cultures, tissues, organs, extracts or secretions, air, water, or soil samples or extracts, or any combination thereof.

Preparation of Samples

In many analyses or diagnostic procedures on liquid samples it may be advantageous to adsorb the sample to a solid surface. This can be done in a number of ways including adding the sample to a well in a microtitre plate, depositing the sample onto a membrane made from materials such as nitrocellulose (NC), nylon, PVDF or any other suitable material, either by direct application or electroblotting following electrophoretic gel fractionation of the sample (Western blotting).

Kits

The present invention also provides kits for detecting or quantifying a target from a sample, wherein the kits facilitate the employment of the particles and methods of the invention. Typically, kits for carrying out an analysis or diagnostic test contain at least a number of the reagents required to carry out the method. Typically, the kits of the invention will comprise one or more containers, containing for example, particles and wash reagents.

In the context of the present invention, a compartmentalised kit includes any kit in which particles and/or reagents are contained in separate containers, and may include small glass containers, plastic containers or strips of plastic or paper. Such containers may allow the efficient transfer of reagents from one compartment to another compartment whilst avoiding cross-contamination of the samples and reagents, and the addition of agents or solutions of each container from one compartment to another in a quantitative fashion. Such kits may also include a container which will accept a test sample, a container which contains the particles used in the assay and containers which contain wash reagents (such as phosphate buffered saline, Tris-buffers, and like).

Typically, a kit of the present invention will also include instructions for using the kit components to conduct the appropriate methods.

Methods and kits of the present invention find application in any circumstance in which it is desirable to detect and/or quantify a component from a sample.

EXAMPLES

Example 1

Creation of a N-Terminal Fusion of GFP to a Chimeric Construct Containing Both a Protein A and Particle Forming Domain The following procedure describes the recombinant fusion of GFP, and eGFP to protein A zz domain, and a P40 Particle Forming Domain (PFD). The gfp gene contains an internal NcoI site that had to be removed to facilitate the transfer of the gfp gene into the NcoI site of an expression vector.

The gfp and egfp genes used for this work contained three point mutations altering residues at positions 72, 153 and 163. These mutations have previously been shown to improve the maturation rate and fluorescence intensity of GFP when expressed in E. coli. The egfp gene has a further point mutation changing residue position 65 (S65A). The S65A modification confers a higher excitation wavelength (488 nm) to the protein, making it more suitable for applications requiring excitation of fluorescence using an Argon laser. The residue changes are summarised in Table 1.

TABLE 1

| Residue positions differences | | | | |
|---|---|---|---|---|
| Position | 65 | 72 | 153 | 163 |
| Native GFP | Ser | Ser | Met | Val |
| Modified GFP | Ser | Ala | Thr | Ala |
| Modified eGFP | Ala | Ala | Thr | Ala |

Elimination of the Internal NcoI Restriction Sites in the gfp and egfp Genes

Figure 6:
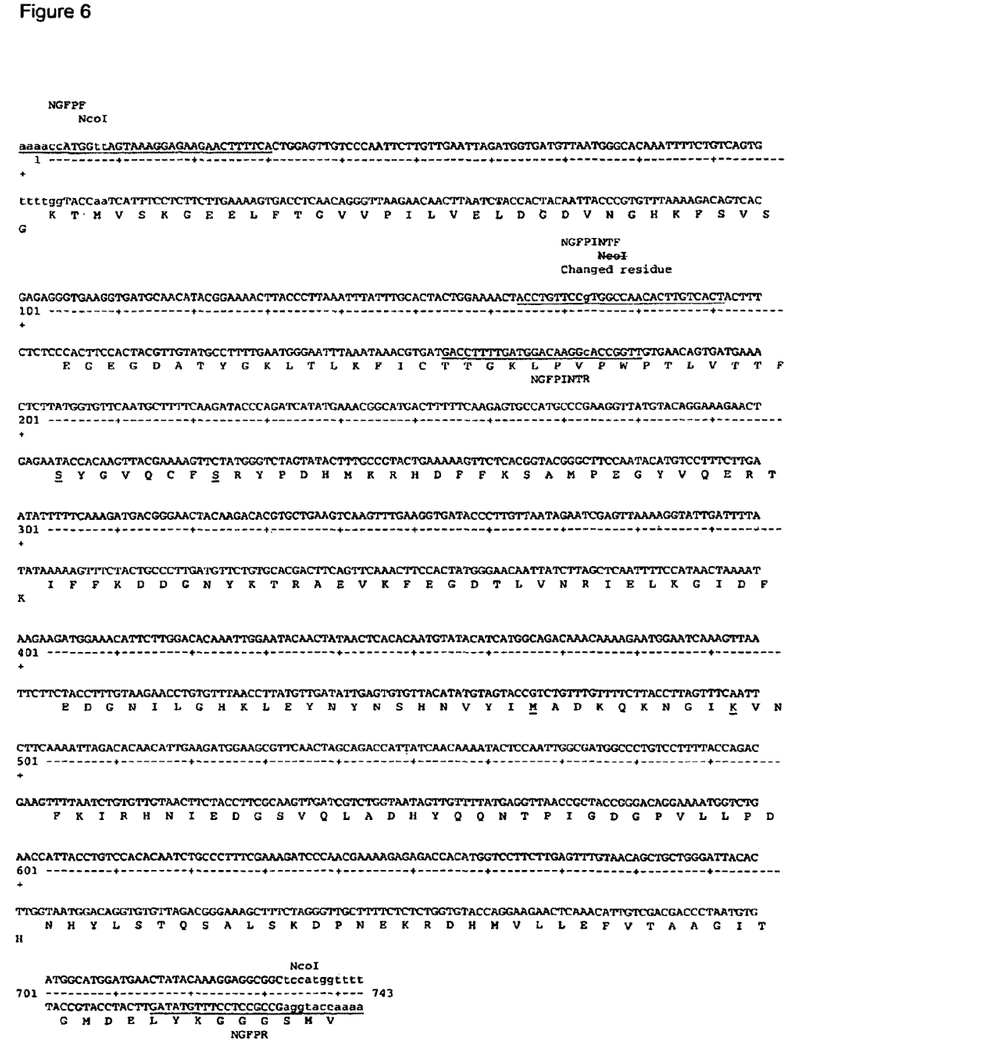
FIG. 6 shows map of gfp gene showing binding sites (underlined) of oligonucleotides as described in Table 2 (nucleotide sequence—SEQ ID NO: 1, peptide sequence—SEQ ID NO: 2).
Figure 7:
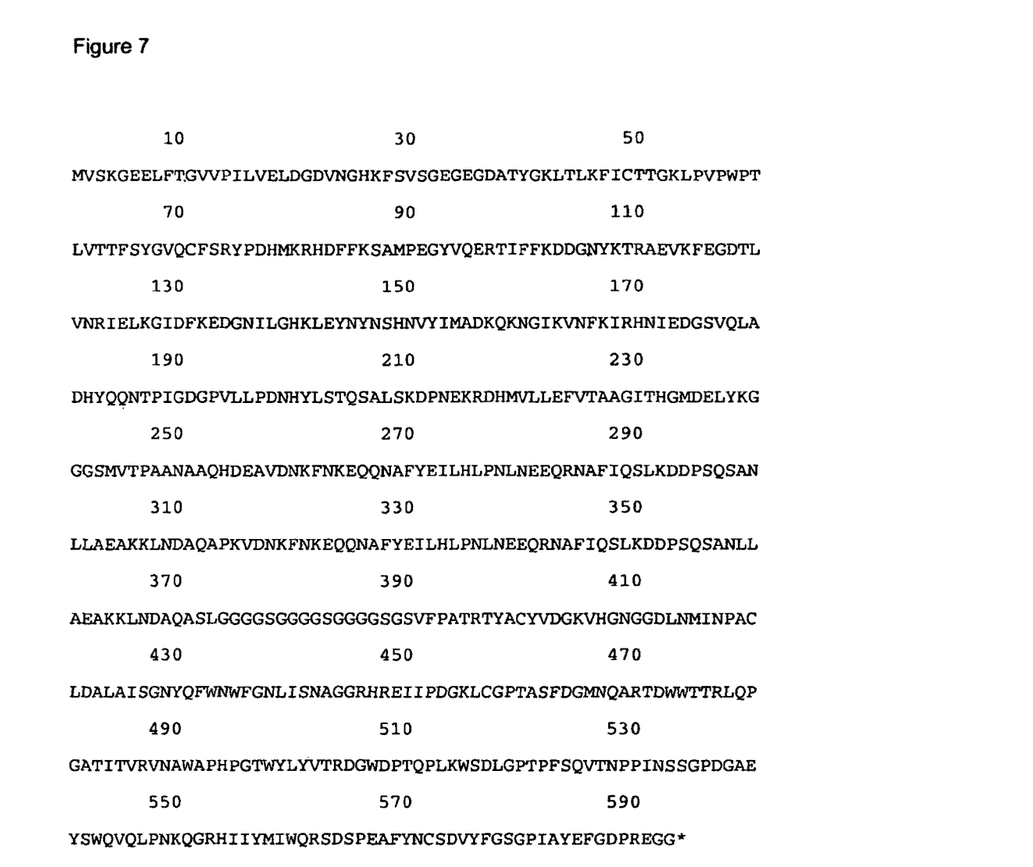
FIG. 7 shows amino acid sequence of predicted translated gene product from pDuet:NGFPNLCP40 (SEQ ID NO: 3).

The region encoding GFP was amplified in two parts by PCR using the primer combinations NGFPF+NGFPINTR (205 bp product) and NGFPINTF+NGFPR (485 bp product). Primer sequences are listed in Table 2, and depicted in FIG. 6. The NGFPINTF and NGFPINTR primers contain a single silent nucleotide change to eliminate the NcoI site present within the gfp open reading frame. The two PCR products were gel-purified, then recombined by overlap extension PCR to reform a GFP gene without an internal NcoI site. The same overlap extension procedure was used to create an egfp gene lacking the internal NcoI site.

The NGFPF and NGFPR primers were each designed to incorporate a NcoI site at each end of each gfp gene to allow NcoI restriction digestion of the full length gfp or egfp PCR product and ligation of the genes into similarly digested plasmid.

TABLE 2

| | Oligonucleotide primers | |
|---|---|---|
| Primer | Sequence | SEQ ID NO: |
| NGFPF 5' | AAAACCATGGTTAGTAAAGGAGAAGAACTTTTCA | 4 |
| NGFPR 5' | AAAACCATGGAGCCGCCTCCTTTGTATAG | 5 |
| NGFPINTF 5' | ACCTGTTCCGTGGCCAACACTTGTCACT | 6 |
| NGFPINTR 5' | TTGGCCACGGAACAGGTAGTTTTCCAG | 7 |

Example 2

Gene Cloning and Expression

NcoI digested gfp and egfp PCR products were ligated into the NcoI site of the vector pDuet:NPANLCP40 to create the plasmids pDuet:NGFPNPANLCP40 and pDuet:NeGFPN-PANLCP40 as depicted in FIG. 2. Ligated DNA was transformed into E. coli strain BL21-Tuner (Novagen). The orientation of the plasmid insert within the vector was determined by colony PCR and by observation of colony fluorescence when illuminated by long wavelength UV light (375 nm). Recombinant transformants were grown in liquid culture (LB medium+100 µg/ml Ampicillin) and plasmid DNA isolated from cells using a Qiagen Spin miniprep kit (Qiagen). Plasmid DNA was sequenced to confirm the gfp or egfp inserts were intact, and correctly oriented.

Figure 1A:
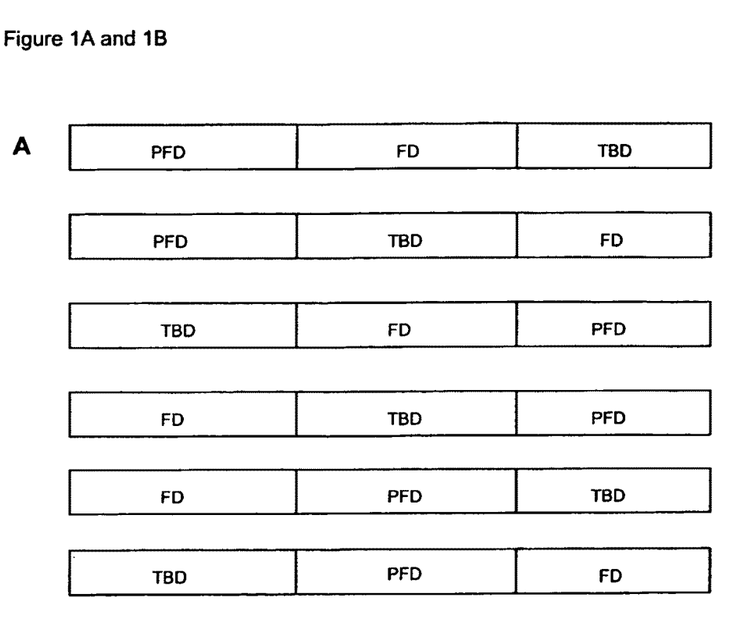
FIG. 1 shows some of the possible combinations of the three protein domains, Particle Forming Domain (PFD), Fluorescent Domain (FD), and Target Binding Domain (TBD). The domains may or may not be interspaced by linking regions. A shows some of the possible combinations when all three domains are linked together in one sequence. B shows one possible combination of two separate sequences when the fluorescent protein particles are made by co-expressing to separate fusion proteins, one which contains a Particle Forming Domain and a Target Binding Domain, and the other which contains a Particle Forming Domain and a Fluorescent Domain.
Figure 1B:
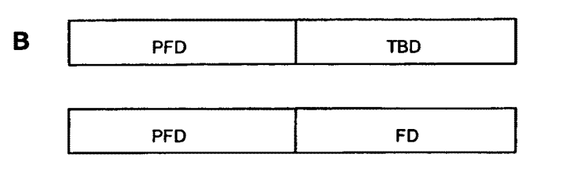
Figure 2A:
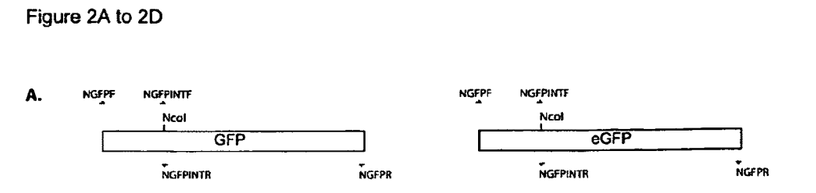
Figure 2B:
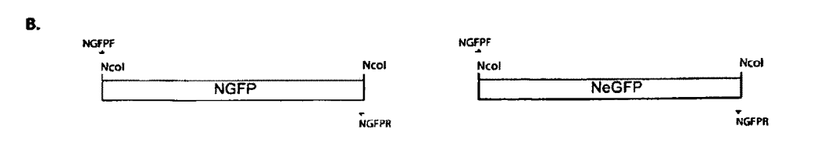
Figure 2C:
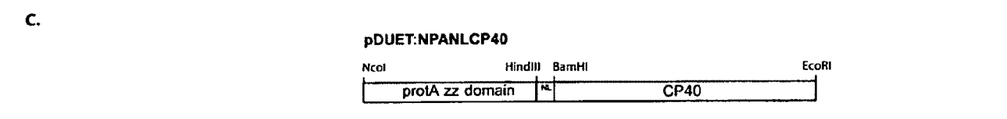
Figure 2D:
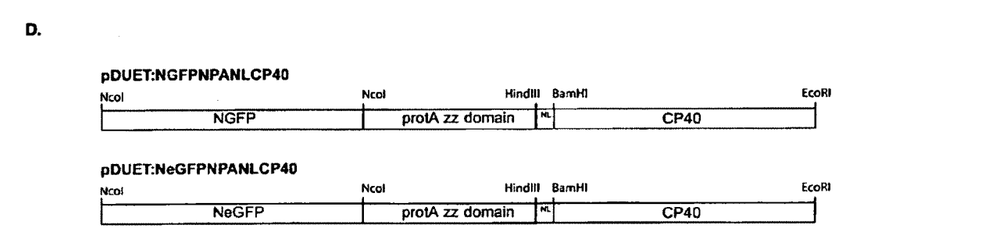
Figure 3:
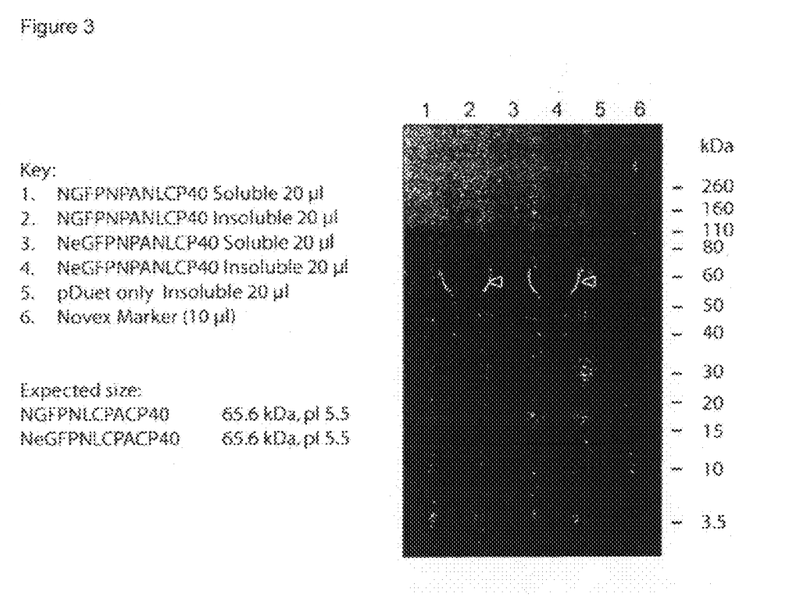
FIG. 3 shows SDS-PAGE of soluble and purified insoluble protein particle fractions of cell lysates. Arrow heads indicate the insoluble recombinant protein.

To prepare recombinant protein, 5 ml overnight cultures of each recombinant isolate were grown in LB medium containing 100 µg/ml ampicillin then used to seed 100 ml of fresh medium containing antibiotic. A control strain containing the plasmid pDuet1 was Each culture was then grown at 37° C. with shaking until the cell density reached an absorbance at 590 nm of approximately 1.5. IPTG was then added at a final concentration of 0.05 mM, and the cells grown a further 3 hours. Cells were harvested by centrifugation, then lysed by two passages through a French pressure cell. Then insoluble fraction of the lysate was harvested by centrifugation at 18,000 rpm for 30 min. The pellet was the fully resuspended in BPER (Pierce) and the protein particles recovered as per the BPER manufacturers recommendations. The expressed protein particle fractions were examined by SDS-PAGE electrophoresis as shown in FIG. 3.

Example 3

Detection of Antibodies

A halving dilution series of rabbit anti-gliadin antibody (Sigma) with a starting concentration of 100 ng/μl was prepared in PBS buffer (137 mM NaCl, 2.7 mM KCl, 10 mM Na$_2$HPO$_4$, 2 mM KH$_2$PO$_4$, 1 mM CaCl$_2$, 0.5 mM MgCl$_2$, pH 7.4). Nunc Maxisorp 96 well microtitre plates were incubated overnight at 4° C. with 100 μl of diluted antibody. Wells were the incubated with 100 μl blocking buffer (5% skim milk, 1% bovine serum albumin fraction V) for 1 hour at room temperature. A series of control wells were prepared without antibody and blocked in the same manner.

Figure 4:
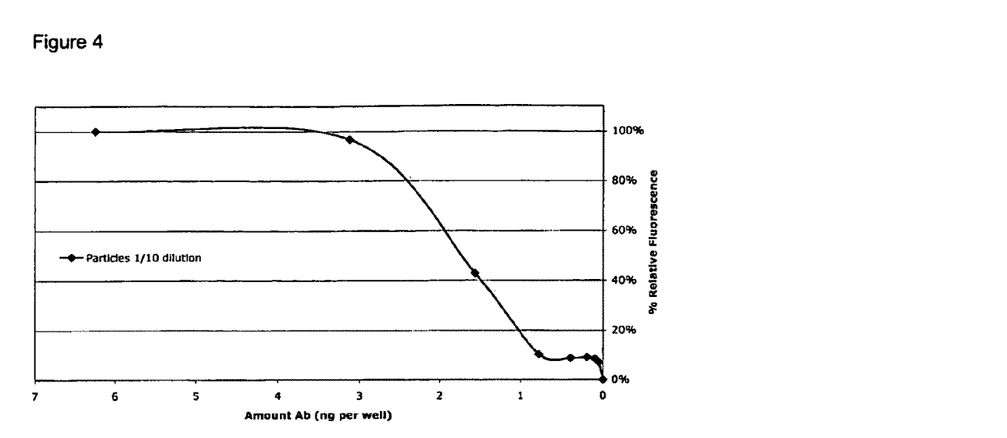
FIG. 4 shows detection of binding of fluorescent NGFPN-PANLCP40 particles to plate-bound rabbit anti-gliadin antibody. This figure shows a graph of the fluorescent signal obtained by using fluorescent protein particles described in example 1 and 2, consisting of a p40 particle forming domain, a protein A target binding domain, and a GFP fluorescent domain to detect rabbit antibody bound to a microtitre plate in concentrations ranging from 0 to 6 ng per well.

A 1/10 dilution of NGFPNPANLCP40 particles in PBS buffer were then applied to the plate and incubated X min at room temperature with gentle mixing. Plates were washed twice in PBS-Tween buffer (PBS buffer containing 0.05% Tween 20), then the fluorescence in each well was measured using a BMG Fluostar Galaxy plate reader with an excitation filter of 405 nm and an emission filter of 520 nm. The data is presented in FIG. 4. No significant signal was detected in the control wells without antibody.

The observed results indicate that the NGFPNPANLCP40 particles bind and are retained in the plate only if the target rabbit anti-gliadin antibody was present in the well. This result indicates that the Protein A domain of the NGFPNPAN-LCP40 particles are binding specifically to the antibody.

Example 4

Detection of Antigen

NGFPNPANLCP40 particles were washed in 1×PBS buffer, pelleted by centrifugation at 13,000 rpm for 1 min in a microcentrifuge, then resuspended in PBS buffer. Rabbit anti-gliadin antibody (150 μl of 5 mg/ml stock solution) was mixed with an equal volume of NGFPNPANLCP40 particles. The mixture was incubated for 45 min at room temperature with gentle rocking to allow binding of the antibodies to the Protein A domains present in the particle. Any unbound antibody was removed by washing the particles twice in PBS-Tween buffer. Briefly, the particles were pelleted by centrifugation as above, resuspended in PBS-Tween buffer, centrifuged again, then resuspended in 300 μl Blocking buffer. These particles are herein referred to as Ab-bound NGFPNPANLCP40 particles.

Figure 5:
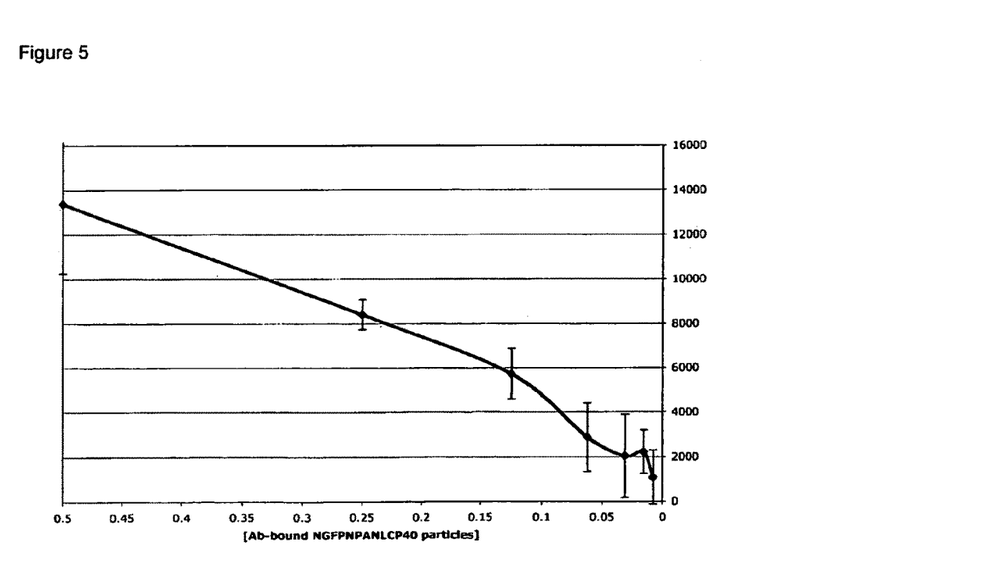
FIG. 5 shows detection of binding of Ab-bound fluorescent NGFPNPANLCP40 particles to plate bound gliadin. This figure shows a graph of the fluorescent signal obtained by using fluorescent particles with protein A as the target binding domain, to which anti-gliadin antibodies have been bound, to detect plate bound gliadin.

Nunc Maxisorp 96 well microtitre plates were prepared and incubated overnight at 4° C. with 125 μg per well of gliadin presolubilised in 1% SDS, 7% beta-mercaptoethanol. The wells were then incubated 1 hour at room temperature with 100 μl Blocking buffer. A halving dilution series of Ab-bound NGFPNPANLCP40 particles was prepared and applied in triplicate to the plate. The plate was then incubated at room temperature with gentle rocking for 1 hour. Plates were then washed twice in PBS-Tween buffer. The fluorescence in each well was then measured using a BMG Fluostar Galaxy plate reader with an excitation filter of 405 nm and an emission filter of 520 nm. The data is presented in FIG. 5.

These results indicate that the complex of gliadin-specific antibody bound 30 NGFPNPANLCP40 particles could bind specifically to gliadin in a near linear concentration dependent manner. The obtained results clearly show that the protein particles according to the present invention can be used for applications that require detection of a target molecule as well as for applications where detection and quantitation of the target molecule are desired.

It will be appreciated by persons skilled in the art that numerous variations and/or modifications may be made to the invention as shown in the specific embodiments without departing from the spirit or scope of the invention as broadly described. The present embodiments are; therefore, to be considered in all respects as illustrative and not restrictive.

The invention claimed is:

1. An insoluble fluorescent protein particle comprising: a particle forming component which forms or aggregates into a substantially insoluble protein particle when expressed by a cell; a fluorescent component; and a functional component capable of binding to, or being bound by, a target.

2. The insoluble fluorescent protein particle according to claim 1 wherein the particle forming component is obtained or derived from a protein that can self assemble into particles when expressed in a cell.

3. The insoluble fluorescent protein particle according to claim 2 wherein the particle forming component is protein p40, alpha-amylase, human alpha-fetoprotein, Somatotropin, cellulose binding domain from clostridium, particle forming parts thereof, or other proteins which form or aggregate into a particle when expressed in a host microorganism.

4. The insoluble fluorescent protein particle according to claim 3 wherein the particle forming component is protein p40 or aggregating part thereof.

5. The insoluble fluorescent protein particle according to any one of claims 1 to 4 wherein the fluorescent component is a fluorescent protein selected from Green Fluorescent Protein (GFP), enhanced Green Fluorescent Protein (eGFP), Blue Fluorescent Protein (BFP), Yellow Fluorescent Protein (YFP), Cyan Fluorescent Protein (CFP), Red Fluorescent Protein (RFP), or combination thereof, or fluorescent parts or derivatives thereof.

6. The insoluble fluorescent protein particle according to claim 5 wherein the fluorescent component is Green Fluorescent Protein (GFP) or a fluorescent part or derivative thereof.

7. The insoluble fluorescent protein particle according to any one of claims 1-4 and 6 wherein the functional component comprises an antibody binding domain, protein A, protein G, protein L, an antibody, an antibody binding domain, a single chain antibody, avidin, streptavidin, an enzyme, an inhibitor, an antigenic determinant, an epitope, a binding site, a lectin, a polyhistidine, an oligohistidine, a receptor, a hormone, a signalling molecule, a polypeptide with specific or group specific binding capabilities, or combination thereof.

8. The insoluble fluorescent protein particle according to claim 7 wherein the functional component is protein A, protein G, protein L or active fragment thereof.

9. The insoluble fluorescent protein particle according to any one of claims 1 to 4, 6 and 8 wherein the target is a ligand, a compound or biological entity, a protein, a peptide, a polypeptide, an immunoglobulin, biotin, an inhibitor, a co-factor, an enzyme, a receptor, a monosaccharide, an oligosaccharide, a polysaccharide, a glycoprotein, a nucleic acid, a hormone, a toxin, a cell or fragment thereof, an organelle, a virus, a bacterium, a fungus, a protist, a parasite, an animal, a plant or substructure, fragments or combinations thereof.

10. The insoluble fluorescent protein particle according to claim 1 comprising an N-terminal GFP-protein A zz domain-linker-C-terminal P40 (NGFPNPANLCP40).

11. A chimeric nucleic acid molecule encoding an insoluble fluorescent protein particle comprising:
a nucleic acid molecule encoding an aggregating protein component which forms or aggregates into a substantially insoluble protein particle when expressed by a cell;
a nucleic acid molecule encoding a fluorescent protein component; and
a nucleic acid molecule encoding a protein functional component capable of binding to, or being bound by, a target.

12. A vector comprising a chimeric nucleic acid molecule according to claim 11.

13. A method of forming an insoluble fluorescent protein particle capable of binding to, or being bound by, the method comprising:
providing a chimeric nucleic acid molecule according to claim 11 or a vector according to claim 12 to a cell; and
allowing the cell to express the nucleic acid molecule to form an insoluble fluorescent protein particle.

14. An insoluble fluorescent protein particle produced by the method according to claim 13.

15. A method for detecting a target in a sample comprising:
providing an insoluble fluorescent protein particle according to any one of claims 1 to 4, 6, 8, 10 and 14 to a sample;
allowing the fluorescent protein particle to bind to a target in the sample; and detecting any fluorescent particles bound to the target in the sample.

* * * * *